United States Patent
Damoc et al.

(10) Patent No.: US 9,865,441 B2
(45) Date of Patent: Jan. 9, 2018

(54) MASS SPECTROMETER

(71) Applicant: Thermo Fisher Scientific (Bremen) GmbH, Bremen (DE)

(72) Inventors: Nicolaie Eugen Damoc, Bremen (DE); Eduard Denisov, Bremen (DE); Dirk Nolting, Bremen (DE); Martin Zeller, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 0 days.

(21) Appl. No.: 14/912,118

(22) PCT Filed: Aug. 21, 2014

(86) PCT No.: PCT/EP2014/067845
§ 371 (c)(1),
(2) Date: Feb. 15, 2016

(87) PCT Pub. No.: WO2015/025008
PCT Pub. Date: Feb. 26, 2015

(65) Prior Publication Data
US 2016/0203964 A1    Jul. 14, 2016

(30) Foreign Application Priority Data
Aug. 21, 2013 (GB) .................... 1314977.8

(51) Int. Cl.
*H01J 49/00* (2006.01)
*H01J 49/04* (2006.01)
(Continued)

(52) U.S. Cl.
CPC ........ *H01J 49/0422* (2013.01); *H01J 49/005* (2013.01); *H01J 49/0031* (2013.01);
(Continued)

(58) Field of Classification Search
CPC ...... H01J 49/0422; H01J 49/005; H01J 49/40; H01J 49/4245; H01J 49/4265; H01J 49/0077; H01J 49/0031; G01N 27/622
(Continued)

(56) References Cited

U.S. PATENT DOCUMENTS

| 4,234,791 A | 11/1980 | Enke et al. |
| 5,248,875 A * | 9/1993 | Douglas ............... H01J 49/005 250/281 |

(Continued)

FOREIGN PATENT DOCUMENTS

WO    2012/116765 A1    9/2012

OTHER PUBLICATIONS

Watson et al., "Introduction to Mass Spectrometry—Instrumentation, Applications and Strategies for Data Interpretation", West Sussex, England, XP055162089, 4th Edition, 2007, pp. 186-187.
(Continued)

*Primary Examiner* — Michael Maskell
(74) *Attorney, Agent, or Firm* — David A. Schell (57) ABSTRACT

The present disclosure provides a mass spectrometer for performing an analysis of sample ions, and a method for operating a mass spectrometer. The mass spectrometer comprises a first ion optical element that is supplied with a first gas; a mass analyzer, wherein the performance of the mass analyzer is dependent on the pressure of the first gas in the first ion optical element; and a controller for setting a property of the first gas, which comprises at least the pressure of the first gas, on the basis of a characteristic of the analysis to be performed by the mass spectrometer.

19 Claims, 7 Drawing Sheets

(51) Int. Cl.
　　　*H01J 49/40* (2006.01)
　　　*H01J 49/42* (2006.01)
　　　*G01N 27/62* (2006.01)

(52) U.S. Cl.
　　　CPC .......... *H01J 49/0077* (2013.01); *H01J 49/40* (2013.01); *H01J 49/4245* (2013.01); *H01J 49/4265* (2013.01); *G01N 27/622* (2013.01)

(58) Field of Classification Search
　　　USPC ................................................ 250/281–283
　　　See application file for complete search history.

(56) References Cited

U.S. PATENT DOCUMENTS

| | | |
|---|---|---|
| 6,774,360 B2 | 8/2004 | Guevremont et al. |
| 6,781,117 B1 * | 8/2004 | Willoughby .......... H01J 49/005 250/281 |
| 2007/0262253 A1 * | 11/2007 | Guo ................... G01N 33/6848 250/283 |
| 2009/0206250 A1 | 8/2009 | Wollnik |
| 2010/0237233 A1 | 9/2010 | Covey et al. |
| 2011/0210241 A1 * | 9/2011 | Badiei .................. G05D 7/0635 250/282 |
| 2012/0032073 A1 * | 2/2012 | Rand ................... H01J 49/0077 250/282 |

OTHER PUBLICATIONS

Mei, et al., "Effects of Target Gas in Collision-Induced Dissociation Using a Double Quadrupole Mass Spectrometer and Radiofrequency Glow Discharge", J Am Soc Mass Spectrom 1994, pp. 845-851.

Vachet, et al., "Effects of Heavy Gases on the Tandem Mass Spectra of Peptide Ions in the Quadrupole Ion Trap", J Am Soc Mass Spectrom 1996 (7), pp. 1194-1202.

* cited by examiner

MASS SPECTROMETER

TECHNICAL FIELD

The present disclosure relates to a mass spectrometer and a method for operating a mass spectrometer.

BACKGROUND

Mass spectrometers typically comprise a number of different ion optical elements with different modes of operation for performing different functions. Examples of the ion optical elements that a mass spectrometer may have include an element for collision induced dissociation (a collision cell), another for intermediate ion storage (such as an RF ion trap) and another for mass analysis.

Each of these different ion optical elements may be implemented using ion traps (for example, RF ion traps and/or other ion trapping devices), but each ion trap will have different pressure requirements in order to perform their different functions. For example, the mass analysis ion trap may need a very low pressure because collisions between ions and residual gas molecules may lead to scattering losses which reduce the signal intensity and sensitivity. However, the collision cell requires a high collision gas pressure, otherwise ions that enter the cell at high kinetic energies will not be trapped, since they must undergo several collisions in order to cool down sufficiently. And the ion trap used for intermediate storage may operate best at a pressure slightly below the collision cell pressure.

Each of the ion traps used for these functions may be connected to each other and gas directly supplied into the highest pressure trap such that the different gas pressures of each trap may not be treated independently from each other. For example, where the collision cell is supplied directly with gas, decreasing the pressure in the collision cell may lead to a decrease in the gas pressure in the intermediate ion storage trap, reducing the trapping efficiency therein, and a decrease in pressure in the mass analysis ion trap, increasing the signal intensity and/or resolution from the mass analysis ion trap. Therefore, the pressure of the ion traps may be a compromise between the different needs of the different ion traps in the device, for example the conflicting needs of trapping efficiency and signal intensity or resolution.

Furthermore, different types of ions may require different pressure regimes in the ion traps. For example, for bigger molecules, such as intact proteins or protein complexes, a gas pressure suitable for small molecules or bottom up proteomics may result in significantly lower sensitivity. A loss of sensitivity might make accurate analysis of results significantly more difficult, if not impossible.

Therefore, the gas pressures in the ion optical elements may also have to be a compromise to achieve the best performance for the most common uses of the mass spectrometer, such as small molecules or bottom up proteomics, at the expense of performance for less common uses.

SUMMARY

The present disclosure relates to a mass spectrometer for performing an analysis of sample ions, the mass spectrometer comprising a first ion optical element that is supplied with a first gas; and a controller for setting a property of the first gas on the basis of a characteristic of the analysis to be performed by the mass spectrometer.

The spectrometer comprises a mass analyser, wherein the performance of the mass analyser is dependent on the pressure of the first gas in the first ion optical element and the setting a property of the first gas includes setting at least the pressure of the first gas. The performance of the mass analyser thus is also varied by varying the pressure of the first gas in the first ion optical element.

Preferably, the characteristic of the analysis to be performed by the mass spectrometer comprises a desired performance of the mass analyser. More preferably, the characteristic of the analysis to be performed by the mass spectrometer comprises at least a desired analysis resolution. The invention desirably utilises a dependence upon the gas pressure and/or gas type of the signal intensity and/or analysis resolution obtained from the mass analyser for sample ions of a given mass range. The setting of gas pressure and/or gas type by the controller thereby enables optimising the signal intensity and/or analysis resolution obtained from the mass analyzer.

Desirably, since the performance of the mass analyser is dependent on the pressure of the first gas in the first ion optical element, setting the property of the first gas is a compromise between optimising the performance of the first ion optical element and optimising the performance of the mass analyser.

The mass analyser is preferably selected from: an ion cyclotron resonance (ICR) mass analyser, an orbital trap mass analyser, a time-of-flight mass analyser (especially a multiple-reflection time-of-flight (MR-TOF) mass analyser), an electrostatic trap mass analyser, an electrodynamic ion trap mass analyzer and a mass filter. The first ion optical element is preferably a collision cell.

The gas supplied to the ion optical element may be referred to herein as a buffer gas. The performance of a mass spectrometer may vary for different types of analysis where the properties, such as composition and pressure, of the buffer gas for an ion optical element of the mass spectrometer are fixed. For example, measurement sensitivity may be optimised for larger molecules by using a different gas pressure in the mass analyser to the optimum gas pressure required for use with smaller molecules. The buffer gas supplied to the ion optical element may be a collision gas (e.g. for a collision cell) and/or a cooling gas (e.g. for an ion store).

Consequently, by considering a characteristic of the analysis to be performed, whether that be one or more physical properties of the sample ions, an application of the analysis to be performed, a desired analysis resolution or some function of at least one of these aspects, a suitable property of the gas for an ion optical element of the mass spectrometer can be set by the controller. The property of the gas may be suitable to, for example, improve the resolution of the analysis by allowing longer transients and/or improve ion trapping efficiency allowing a greater signal, better sensitivity and/or improved resolution in the analysis, thus improving the performance that can be achieved across a variety of different characteristics of analysis compared with a mass spectrometer set up where the properties of the gas are fixed.

The controller preferably comprises a computer that enables automatically setting a property of the first gas (and where applicable a second gas as hereafter described), especially on the basis of input information about a characteristic of the analysis to be performed by the mass spectrometer. The information may be input by an operator, for example via a user interface or a programming tool, and the controller uses the information to set the property of the gas. The controller preferably contains information relating to types of analysis to be performed by the mass spectrometer and associated properties of the gas that should be set. The information may be contained in the controller in software or firmware. The controller is preferably interfaced to a pressure controller, such as a valve, and/or to a gas type selector. The controller thus preferably controls a pressure controller and/or a gas type selector, e.g. through software or firmware to apply the property of the gas to the ion optical element.

The property of the first gas may comprise at least one of a first gas pressure in the first ion optical element and a composition of the first gas. Therefore, the controller can adjust the gas pressure in the ion optical element, or the composition of the gas (for example, the type of gas used for supplying the ion optical element), or both the gas pressure and the composition of the gas, depending upon the characteristic of the analysis to be performed by the mass spectrometer. A feed back line is preferably provided to control the gas pressure in the ion optical element, wherein the feed back line comprises a pressure controller, such as a valve (as described above) in the gas supply, and a pressure gauge preferably positioned in the ion optical element and also interfaced to the controller. The partial pressure of the first gas in the mass analyser is preferably determined, e.g. by pressure gauge measurement, and the determined pressure in the mass analyser is received by the controller (pressure gauge preferably is interfaced to the controller) and is used in setting the pressure of the first gas in the ion optical element.

The ion optical element (first or second ion optical element) may be supplied directly from a gas source, or indirectly via a second ion optical element that is supplied directly from a gas source and is connected to the first ion optical element. For example, where an ion trap is connected to a collision cell, the collision cell may be directly connected to a gas supply and directly supplied with gas. The ion trap may be indirectly supplied with the gas by virtue of its connection to the collision cell. Likewise, where there is a further ion optical element, e.g. a mass analyser, connected to the ion trap, it too is indirectly supplied with gas by virtue of its connection to the collision cell via the ion trap.

In one type of embodiment, the mass spectrometer may comprise a mass analyser, an ion trap and a collision cell, wherein the collision cell is connected to the ion trap and the ion trap is further connected to the mass analyser. The ion trap may act as an intermediate ion store. In one example of such an embodiment, the collision cell is supplied directly with a first gas to a first gas pressure (since the collision cell has the highest pressure of the mass analyser, ion trap and collision cell), the ion trap supplied indirectly with the first gas by virtue of its connection to the collision cell and the mass analyser supplied indirectly with the first gas by virtue of its connection to the ion trap. The mass analyser may be the first ion optical element such that the controller sets a first gas pressure in the mass analyser on the basis of a characteristic of the analysis to be performed by the mass spectrometer.

Where the first ion optical element is not supplied directly from the gas source, the gas pressure in the ion optical element will be dependent on the gas pressure of the directly supplied ion optical element, and may be controlled by adjusting the gas pressure supplied to the directly supplied ion optical element (for example, by using a valve in the gas supply line).

The mass spectrometer may further comprise a second ion optical element that is supplied with a second gas; wherein the controller is configured for setting a property of the second gas on the basis of the characteristic of the analysis to be performed by the mass spectrometer. The second ion optical element may be directly or indirectly supplied with the second gas.

For example, the mass spectrometer may comprise a mass analyser, an ion trap and a collision cell, wherein the collision cell is supplied with a first gas to a first gas pressure and the ion trap and mass analyser are supplied independently with a second gas to a second gas pressure (for example, by direct supply to the ion trap and thereby indirect supply to the mass analyser by virtue of its connection to the ion trap). For some applications and sample types, the performance of the mass spectrometer may benefit from the use of a different gas in the mass analyser to the gas used in the collision cell. Furthermore, the performance of the mass spectrometer may also, or alternatively, benefit from a mass analyser gas pressure that might not be attainable in conjunction with an optimal collision cell pressure if the collision cell were directly supplied with gas and the ion trap and mass analyser indirectly supplied via the collision cell (in which case, the gas pressure of the mass analyser would be dependent on the gas pressure of the collision cell).

Much like the first gas, the property of the second gas may comprise at least one of a second gas pressure in the second ion optical element and a composition of the second gas.

The characteristic of the analysis to be performed by the mass spectrometer may be based on at least one of an application of the analysis of the sample ions (for example, "metabolomics", "top down proteomics" "native MS" etc), a type of the sample ions (for example, "bile", "digested cell lysate", "water", etc), an expected mass of the ions, an expected charge of the ions, an expected mass to charge ratio (m/z) of the ions and a desired analysis resolution. For example, the characteristic may be the expected mass of the ions that is input to the controller by an operator of the mass spectrometer. Or, it may, for example, be a function of the expected mass and the expected charge of the ions that are both input by the operator, such as an expected m/z of the ions. Or, it may, for example, be an application of the analysis as the sample ions (such as "metabolomics", "bottom up proteomics" or "top down proteomics") that has been selected by the operator from a list of different applications. Or, it may, for example, be a function of an application of the analysis of the sample ions in combination with at least one expected property of the sample ions, such as mass, charge and/or m/z.

In this way, the operator (i.e. the user) may be presented with a host of different options for the input of information relating to the analysis to be performed and the controller may make a decision regarding the properties of the buffer gas on the basis of the characteristic determined from the information provided by the operator. This may result in an improvement in the performance of the mass spectrometer through application of more suitable gas properties to the ion optical element on the basis of the information that the operator has provided. The operator is also not overburdened by the need to make any calculations or obtain any data not already available to them and may instead simply provide any or all information they have relating to the analysis, for example the type of the sample ions and/or the application of the analysis and/or the expected properties of the sample ions (such as mass and/or charge) if available to them.

Rather than the operator inputting the type of the sample ions, the expected mass of the ions and/or the expected charge of the ions into the controller, the controller may instead determine at least one of these details from a mass spectrometer experimentation result. The result could be an instantaneous measurement of mass and/or charge and/or any other physico-chemical property such as ion mobility, or an average of mass and/or charge and/or other physic-chemical property measurements over a period of time, or a determination of the type of the sample ions from instantaneous or averaged mass spectrometer measurements. Thus, the property of the gas may initially be set to a default property for performing the mass spectrometer experimentation and the gas property set on the basis of the determined characteristic of the analysis to be performed that is based on information obtained by the experimentation. By obtaining the information in this way, the characteristic of the analysis may be determined without any (or just minimal) input from the operator.

The controller may also be configured such that the characteristic of the analysis (regardless of how it was first determined) is updated or adjusted during operation of the mass spectrometer using the same technique of considering instantaneous or average mass and/or charge and/or other physico-chemical property measurements, and the gas property reset according to the updated characteristic. In this way, the accuracy of the characteristic of the analysis to be performed may be improved during operation of the mass spectrometer, thus improving the performance of the mass spectrometer by setting a more suitable gas property.

It can be seen that an aspect of the present disclosure relates to a rules-based approach to controlling the property of the gas that allows for optimising the performance of the mass analyser, preferably as a compromise between performance of the mass analyser and performance of the ion optical element that is supplied with the gas (e.g. a collision cell), and optionally the trapping efficiency in an ion trap that is connected to the ion optical element (the mass analyser may be connected to the ion trap in that case).

The present disclosure in another aspect relates to a mass spectrometer for performing an analysis of sample ions, the mass spectrometer comprising a first ion optical element that is supplied with a first gas; and a controller comprising a computer for making rules-based decisions for setting a property of the first gas, preferably at least the pressure of the first gas, in the first ion optical element. The rules-based decisions are made on the basis of a characteristic of the analysis to be performed by the mass spectrometer.

The rules-based decisions may be made on the basis of one or more of the following as examples:
  a. a desired mass resolution
  b. a general class of ions that the sample ions belong to, which may be the chemical class or type, such as e.g. protein, peptide, "native" protein
  c. a mass of the sample ions
  d. a charge of the sample ions
  e. both mass and charge of the sample ions, e.g. mass-to-charge ratio Preferably, the mass spectrometer comprises a mass analyser as herein described. The rules-based decisions on setting the property of the gas may comprise determining which of a plurality of predetermined mass ranges (more preferably three or more mass ranges) the expected or determined mass of the sample lies within, optionally determining whether a desired mass resolution lies below or above a mass resolution threshold and setting a property of the gas (preferably pressure and/or type, i.e. composition) that will enable a desired signal intensity and/or mass resolution to be obtained using the mass analyzer.

For example, the rules-based decisions on setting the property of the gas may comprise:

i) if the expected or determined mass of the sample ions is below a first mass threshold then set a first pressure of the gas, optionally select a first type of gas;
  ii) if the expected or determined mass of the sample ions is not below the first mass threshold but not above a second mass threshold higher than the first mass threshold then set a second pressure of the gas that is lower than the first pressure, optionally select the first type of gas if a desired mass resolution is below a mass resolution threshold and if a desired mass resolution is not below a mass resolution threshold optionally select a second type of gas, that is lighter than the first type;
  iii) if the expected or determined mass of the sample ions is above the second mass threshold then set a third pressure of the gas that is higher than the first pressure, optionally select a third type of gas that is heavier than the first type.

The first ion optical element may be any one of a mass analyser; a collision cell; an ion storage device; an ion guide; a mass filter; an ion mobility analyser; and an ion lens. Likewise, where there is a second ion optical element, it may be any one of a mass analyser; a collision cell; an ion storage device; an ion guide; a mass filter; and an ion lens. The performance of any ion optical element that is supplied, either directly or indirectly, with a gas may be improved with a selection of the gas composition and/or the gas pressure on the basis of a characteristic of the analysis to be performed by the mass spectrometer.

The present disclosure also relates to a method for operating a mass spectrometer, the method comprising the steps of: determining a characteristic of the analysis to be performed by the mass spectrometer; and setting, on the basis of the characteristic of the analysis to be performed by the mass spectrometer, a property of a first gas used as a buffer gas in a first ion optical element of the mass spectrometer.

The mass spectrometer comprises a first ion optical element and a mass analyser. The performance of the mass analyser is dependent on the pressure of the first gas in the first ion optical element and the setting a property of the first gas includes setting at least the pressure of the first gas. The performance of the mass analyser thus is also varied by varying the pressure of the first gas in the first ion optical element.

Preferably, the characteristic of the analysis to be performed by the mass spectrometer comprises a desired performance of the mass analyser. More preferably, the characteristic of the analysis to be performed by the mass spectrometer comprises at least a desired analysis resolution. The invention desirably utilises a dependence upon the gas pressure and/or gas type of the signal intensity and/or analysis resolution obtained from the mass analyser for sample ions of a given mass range. The setting of gas pressure and/or gas type by the controller thereby enables optimising the signal intensity and/or analysis resolution obtained from the mass analyzer.

Desirably, since the performance of the mass analyser is dependent on the pressure of the first gas in the first ion optical element, setting the property of the first gas is a compromise between optimising the performance of the first ion optical element and optimising the performance of the mass analyser.

The mass analyser is preferably selected from: an ion cyclotron resonance (ICR) mass analyser, an orbital trap mass analyser, a time-of-flight mass analyser (especially a multiple-reflection time-of-flight (MR-TOF) mass analyser), an electrostatic trap mass analyser, an electrodynamic ion trap mass analyzer and a mass filter. The first ion optical element is preferably a collision cell.

As described above in respect of the mass spectrometer apparatus, setting a property of the gas, for example the pressure of the gas in the first ion optical element and/or the composition of the first gas, on the basis of a characteristic of the analysis to be performed by the mass spectrometer can improve the performance of the mass spectrometer. For example, it may improve the resolution of the analysis by allowing longer transients and/or it may improve ion trapping efficiency enabling a greater signal strength and better sensitivity in the analysis and/or it may improve fragmentation efficiency in a collision cell and/or it may avoid unwanted fragmentation in a collision cell and/or it may improve ion mobility resolution in an ion mobility analyser.

The method may further comprise a step of: setting, on the basis of the characteristic of the sample ion, a property of a second gas used for supplying a second ion optical element of the mass spectrometer. As explained above, where two or more different optical ion elements are independently supplied with gas, setting the gas properties for each independently supplied optical ion element can even further improve the performance of the mass spectrometer.

Again, as earlier explained, the characteristic of the analysis to be performed by the mass spectrometer can be based on at least one of an application of the analysis of the sample ions, a type of the sample ions, an expected mass of the sample ions, an expected charge of the sample ions and a desired analysis resolution. For example, it may be a function of at least one of the application of the analysis of the sample ions, the type of the sample ions, the expected mass of the sample ions, the expected charge of the sample ions and a desired analysis resolution.

Furthermore, at least one of the application of the analysis of the sample ions, the type of the sample ions, the expected mass of the sample ions, the expected charge of the sample ions, an expected mass to charge ratio (m/z) of the ions and a desired analysis resolution may be received by the controller from an input of an operator of the mass spectrometer and/or the controller may determine at least one of the type of the sample ions, the expected mass of the sample ions and the expected charge of the sample ions from a mass spectrometer experimentation result. The result could be an instantaneous measurement of mass and/or charge, or an average of mass and/or charge measurements over a period of time, or a determination of the type of the sample ions from instantaneous or averaged mass spectrometer measurements. Thus, the property of the gas may initially be set to a default property for performing the mass spectrometer experimentation and the gas property set on the basis of the determined characteristic of the analysis to be performed that is based on information obtained by experimentation. By obtaining the information in this way, the characteristic of the analysis may be determined without any (or just minimal) input from the operator.

The characteristic of the analysis (regardless of how it was first determined) may also be updated or adjusted during operation of the mass spectrometer using the same technique of considering instantaneous or average mass and/or charge measurements, and the gas property reset according to the updated characteristic. In this way, the accuracy of the characteristic of the analysis to be performed may be improved during operation of the mass spectrometer, thus improving the performance of the mass spectrometer by setting a more suitable gas property.

The first ion optical element may be any one of a mass analyser; a collision cell; an ion storage device; an ion guide; a mass filter; and an ion lens. Likewise, where there is a second ion optical element, it may be any one of a mass analyser; a collision cell; an ion storage device; an ion guide; a mass filter; and an ion lens.

BRIEF DESCRIPTION OF THE DRAWINGS

A mass spectrometer according to an aspect of the present disclosure is described herein by way of example only with reference to the following drawings, in which.

DETAILED DESCRIPTION

Figure 1:
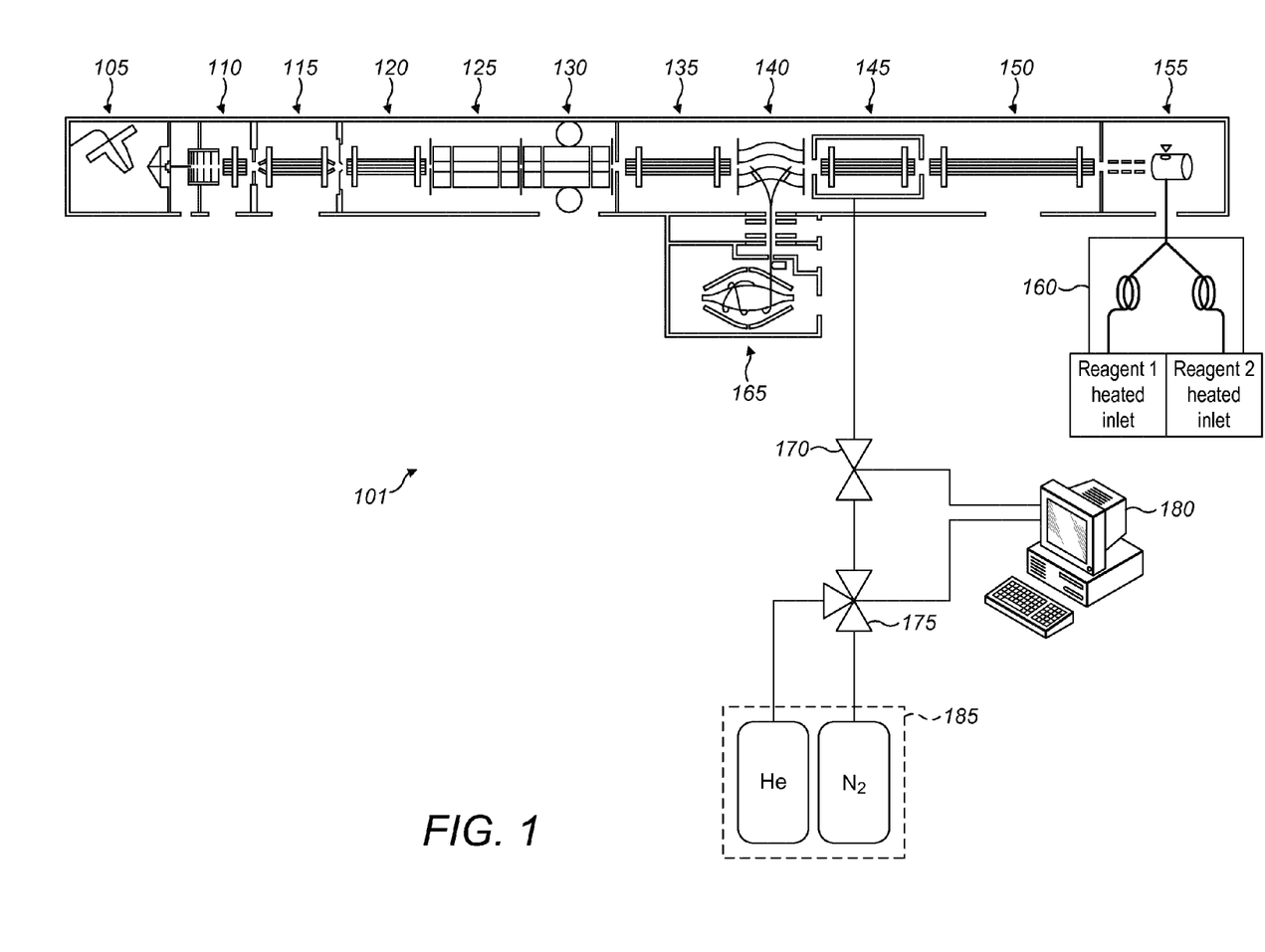
FIG. 1 shows a mass spectrometer comprising a collision cell, an intermediate ion trap and a mass analyzer, wherein buffer gas is supplied to the collision cell via a gas type selector and a pressure controller, the gas type selector and pressure controller being controlled by a controller.

FIG. 1 shows a mass spectrometer 101 comprising multiple elements, including an electrospray ion source 105, a lens arrangement 110, quadrupole with a beam blocker arrangement 115, an octopole 120, a high pressure cell 125, a low pressure cell 130, a mass filter arrangement 135, a curved ion trap (C-trap) 140, a higher-energy collision dissociation (HCD) cell 145, a transfer multipole 150, a reagent ion source 155, reagent inlets 160, a mass analyser 165, a pressure controller 170, a gas type selector 175, a controller 180 and a gas supply 185 comprising a supply of a plurality of different buffer gases, for example helium (He), nitrogen (N2) and xenon (Xe). The HCD cell 145, C-trap 140 and mass analyser 165, as well as other elements of the mass spectrometer 101, are connected to a vacuum system (not shown). The mass analyser 165 in this example is an electrostatic orbital trap (ORBITRAP™).

The gas type selector 175 is configured to enable the controller 180 to select which of the gases in the gas supply 185 should be supplied and the pressure controller 170 is configured to control the pressure to which the gas fills the HCD collision cell 145. Because the HCD collision cell 145 is connected to the C-trap 140, which is in turn connected to the mass analyser 165, the gas used to supply the HCD collision cell 145 will transmit to the C-trap 140 and the mass analyser 165 and be the buffer gas in those elements as well. As such, the HCD collision cell 145 is directly supplied by virtue of its direct connection to the gas supply 185, and the C-trap 140 and mass analyser 165 are indirectly supplied via the HCD collision cell 145.

The pressure to which the HCD collision cell 145 is supplied will affect the gas pressure in the C-trap 140 and the mass analyser 165. The controller 180, which may be a personal computer, controls the gas type selector 175 and the pressure controller 170, which may be a valve, to set the gas used and the pressure to which the HCD collision cell 145 is supplied (and also by extension the C-trap 140 and mass analyzer 165).

Figure 2:
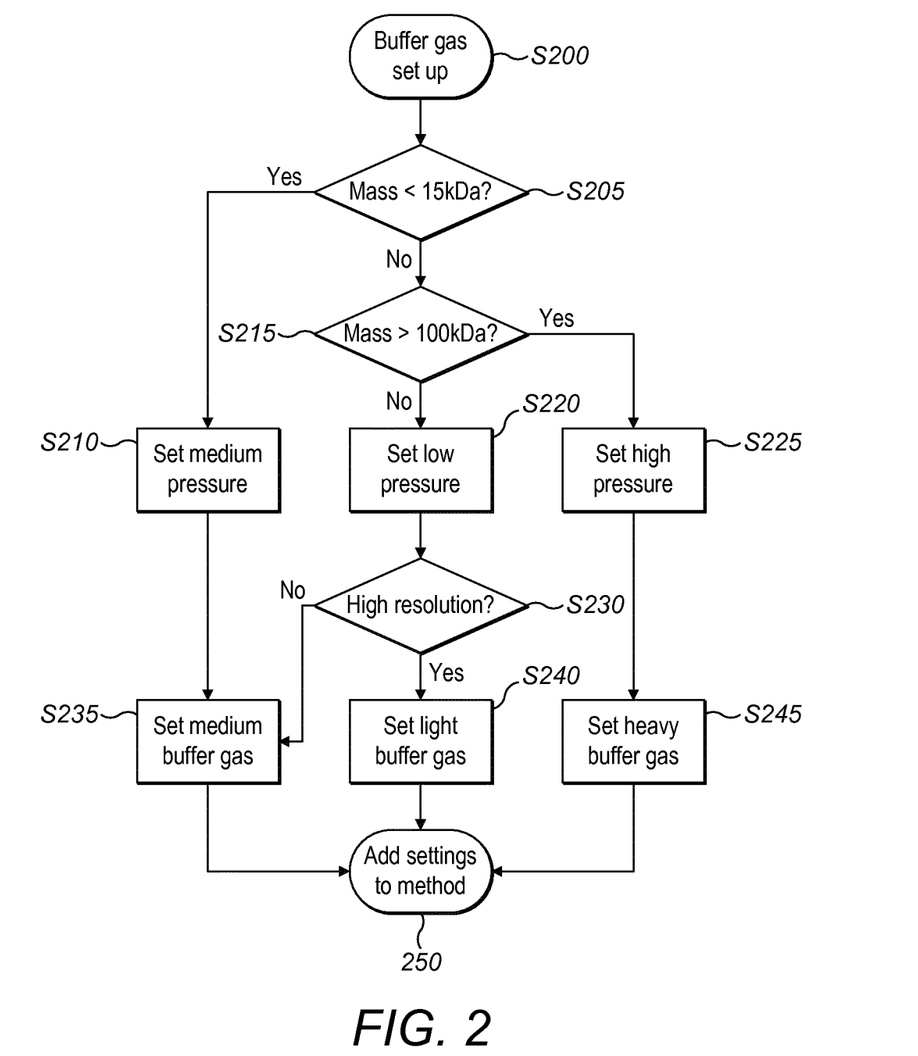
FIG. 2 shows method steps for setting a suitable gas type and gas pressure for the mass spectrometer of FIG. 1.

FIG. 2 shows a control process executed by the controller 180 to select a gas from the gas supply 185 and select a gas pressure for the mass analyser 165. In Step S200, an operator of the mass spectrometer 101 inputs into the controller 180 the application of the analysis to be performed. This may be selected by the operator from a list of different options that might include, for example, "general", "metabolomics", "bottom up proteomics", "top down proteomics" and "native MS".

From this information, the controller 180 can predict the expected mass of the sample ions, for example by looking up on a database an expected mass for the selected application and establish a characteristic of the analysis to be performed by the mass spectrometer 101. The database information may have been obtained previously by any suitable means, for example from previous experimental data and statistical analysis.

Having established an expected mass of the sample ions, it is determined in which expected mass range the expected mass of the sample ions lie. It has been determined from experimental data and mathematical analysis that particular types of buffer gas and gas pressures of the mass analyser 165 can be used to obtain high quality results for particular mass ranges of one to two orders of magnitude. Therefore, by setting particular expected mass ranges with an associated buffer and gas pressure and determining in which expected mass range the expected mass of the sample ions lies, a suitable gas composition and gas pressure can be set for the mass analyser 165 that are known to improve the performance of the mass spectrometer 101 for that expected mass range.

To determine in which expected mass range the expected mass of the sample ions lies, the expected mass is compared to a first threshold value, for example 15 kDa, in Step S205. If the expected mass is less than the first threshold value, the sample ion is considered to be in a low expected mass range and the characteristic of the analysis to be performed is a low expected mass range. The control process then progresses to Step S210 where a suitable pressure is set.

The gas pressure of the mass analyser 165 comprises two components, the base pressure and the partial pressure. The base pressure is the lowest pressure that the mass analyser 165 reaches without any buffer gas. The partial pressure is the pressure of the buffer gas in the mass analyser 165. Therefore, the pressure set by the controller 180 and the pressure controller 170 involves determining the partial pressure.

In Step S210, a medium partial pressure is set for the mass analyser 165, which may be a pressure of between $2.0\text{-}5.0\times10^{-11}$ mbar, for example $3.0\times10^{-11}$ mbar. Partial pressures within this pressure range have been determined by experimentation and theoretical analysis to result in an improved performance for low range expected mass of the sample ions. As explained earlier, the gas pressure in the HCD collision cell 145, the C-trap 140 and the mass analyser 165 are all dependent on each other due to their interconnection. A medium partial pressure has been found to result in the optimum compromise between trapping efficiency in C-trap 140, which is improved by higher gas pressures and results in higher signal intensity, transient decay in the mass analyser 165, which is slowed down by lower partial pressures and results in higher resolution and intensity, and fragmentation efficiency in the HCD collision cell 145, which is improved by higher pressures.

If it is determined in Step S205 that the expected mass of the sample ions is not less than the first mass threshold, the control process progresses to Step S215, where it is determined if the expected mass of the sample ions is greater than a second mass threshold, for example 100 kDa. If the expected mass of the sample ions is not greater than the second mass threshold, the expected mass of the sample ions is considered to lie within a medium expected mass range and the characteristic of the of the analysis to be performed is a medium expected mass range. The control process then progresses to Step S220 where a suitable pressure is set.

In Step S220, a low partial pressure is set for the mass analyser 165, which may be a pressure of between $0.5\text{-}2.0\times10^{-11}$ mbar, for example $1.0\times10^{-11}$ mbar. Partial pressures within this pressure range have been determined by experimentation and theoretical analysis to result in improved performance for low range expected mass. As the mass of the ions increases, the transient decay rate in the mass analyser 165 gets faster due to an increased collision cross section resulting in lower intensity of measurements. When the ion mass increase above a certain level, for example the first threshold and is in the medium expected mass range, a reduction in gas pressure will reduce the trapping efficiency of the C-trap 140, which reduces signal intensity, but also reduces the transient decay rate in the mass analyser 165, resulting in a longer transient life time and therefore increased signal intensity and resolution. The positive effect on mass analyser 165 performance exceeds the negative effect on the C-trap 140, resulting in an improved mass spectrometer performance.

If it is determined in Step S215 that the expected mass of the sample ions is greater than the second mass threshold, the expected mass of the sample ions is considered to lie within a high expected mass range and the characteristic of the analysis to be performed is a high expected mass range. The control process then progresses to Step S225 where a suitable pressure is set.

In Step S225, a high partial pressure is set for the mass analyser 165, which may be a pressure of at least $5.0\times10^{-11}$ mbar, for example $6.0\times10^{-11}$ mbar. Partial pressures within this pressure range have been determined by experimentation and theoretical analysis to result in improved performance for the high expected mass range. An increase in partial pressure compared with low and medium expected mass ranges has been found beneficial because above certain mass values (for example, the second mass threshold) it becomes much more difficult to resolve the ions, so it is often not worthwhile striving for the longer transients and higher resolution that lower partial pressures may bring. This is because the frequencies of close-by ions, separated 1 m/z apart, are equally spaced, but for higher masses the frequency distances become increasingly small. This leads to interference with more pronounced beat patterns, where an intense "beat" reading is followed for a number of seconds by a zero reading before a further intense "beat" reading is detected. When the decay rate is such that the detection of the second beat is very difficult, if not impossible, it is preferable to sacrifice the improved resolution that lower partial pressures may bring and detect the envelope of the isotropic pattern at lower resolution with a short transient by increasing the partial pressure. Therefore, a high partial pressure is set in Step S225 in order to improve the trapping efficiency in the C-trap to thereby provide a greater signal strength and therefore better sensitivity in the mass analyser, and to improve the fragmentation efficiency in the HCD collision cell 145.

Having set a suitable partial pressure, the control process then selects a suitable buffer gas for supplying into the HCD collision cell 145, and by extension into the C-trap 140 and the mass analyser 165 by virtue of indirect supply. Different characteristics of the analysis to be performed will benefit from the use of different buffer gases, so selecting a suitable buffer gas can improve the quality of the analysis results.

Where the expected mass of the sample ions is determined in Step S205 to be in the low range expected mass range, after selecting a medium partial pressure in Step S210, the control process progresses to Step S235 where a medium weight buffer gas from the gas supply 185 is selected. The medium weight buffer gas might be nitrogen ($N_2$) or argon (Ar) and is chosen because it has been determined by experimentation and theoretical analysis to result in the optimum compromise between the conflicting trapping, transient decay and fragmentation efficiency requirements of the C-trap 140, the mass analyser 165 and the HCD collision cell 145 and therefore provide the best performance of the mass analyser 165 for the low expected mass range when at a medium partial pressure (as described above) in the mass analyser 165.

Likewise, when the expected mass of the sample ions is determined in Step S215 to be in the high expected mass range and a high partial pressure is set in Step S225, the control process progresses to Step S245, where a heavy weight buffer gas from the gas supply 185 is selected. The heavy weight buffer gas might be xenon (Xe) or krypton (Kr) and is chosen because it serves further to improve the trapping efficiency of the C-trap 140 and the fragmentation decay of the collision cell 165, thus improving the performance of the mass analyser 165 for the high expected mass range when at a high partial pressure (as described above) in the mass analyzer 165.

When the expected mass of the sample ions is determined in Step S215 to be in the medium expected mass range and a low partial pressure is set in Step S220, the control process progresses to Step S230. In Step S230, the operator of the mass spectrometer is prompted to indicate whether or not they would like to undertake a high resolution analysis of the sample. For some applications where time is limited, for example for chromatography or where many points are to be sampled in MS-imaging, the operator may choose a low-resolution analysis because it requires less time to complete. However, where time is not limited or is less critical and the operator desires a higher resolution analysis, they may choose a high resolution analysis in Step S230.

Where a low-resolution analysis is selected, the control process progresses to Step S235 where, as explained above, a medium weight buffer gas from the gas supply 185 is selected. The medium weight buffer gas provides improved trapping efficiency in the C-trap 140, improving signal intensity, and improved fragmentation efficiency in the HCD collision cell 145, but faster transient decay in the mass analyser 165, reducing resolution. Where a high-resolution analysis is selected, the control process progresses to Step S240 where a light weight buffer gas, for example, helium (He) or hydrogen ($H_2$), from the gas supply 185 is selected, which reduces trapping efficiency in the C-trap 140, decreasing signal intensity, and reduced fragmentation efficiency in the HCD collision cell 145, but slows transient decay in the mass analyzer 165, increasing resolution.

Having determined in which expected mass range the expected mass of the sample ions lies and set the corresponding partial pressure and buffer gas, the control process progresses to Step S250, where the controller 180 applies the set partial pressure and buffer gas by using the gas type selector 175 and the pressure controller 170. The partial pressure may be controlled by the controller 180 using a pressure gauge located in the mass analyser 165, wherein the reading from the pressure gauge is fed back to the controller 180 to complete closed loop control such that the controller may make any necessary adjustments to the pressure controller 170 to achieve the desired partial pressure in the mass analyzer 165.

Having applied the set buffer gas and the partial pressure, the mass spectrometer 101 may undertake analysis of the sample.

Figure 3A:
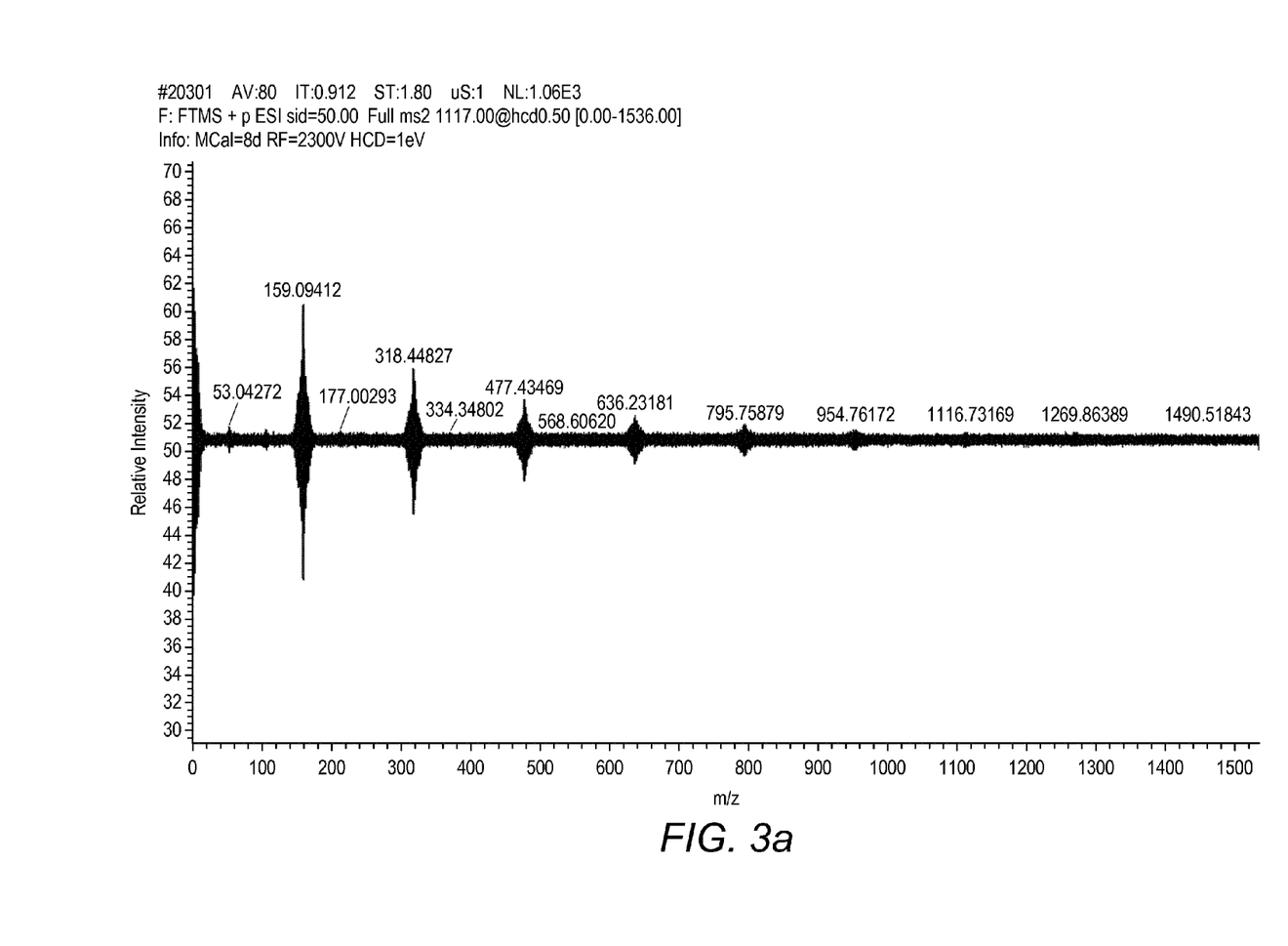
FIGS. 3a and 3b show an analysis of transients carried out using the mass spectrometer of FIG. 1 with different buffer gases.

FIG. 3a shows an analysis of the transients acquired for a 25+ charge state of carbonic anhydrase where nitrogen is used as the buffer gas.

Figure 3B:
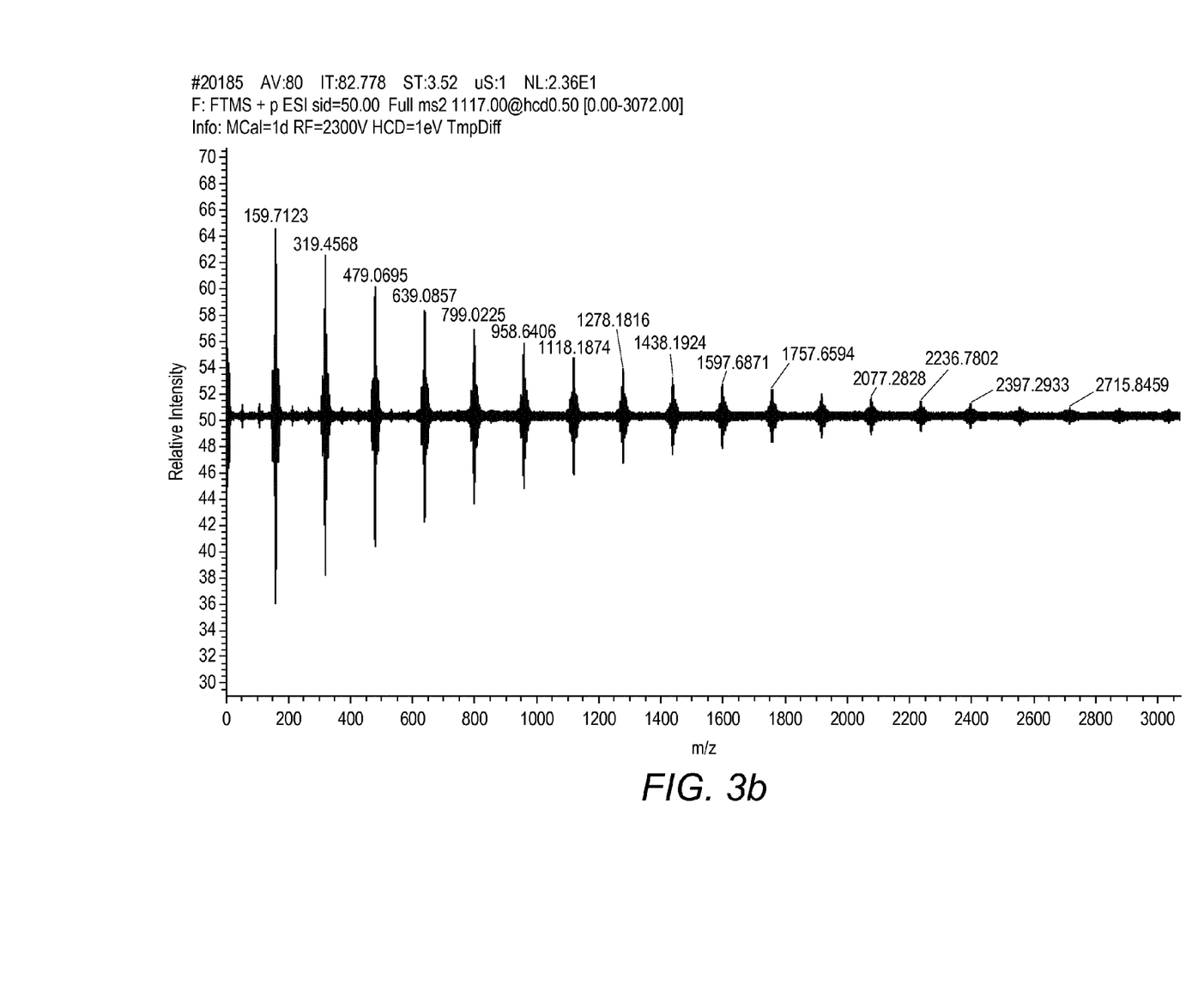

FIG. 3b shows the same analysis of the transients acquired for a 25+ charge state of carbonic anhydrase, but where helium is used as the buffer gas.

Analysis of carbonic anhydrase is a top down proteomic analysis and, as such, falls into the medium expected mass range according to the control process described above. Consequently, the partial pressure is set to a value within the low partial pressure range and the buffer gas used is a light weight buffer gas when the operator desires a high resolution analysis or a medium weight buffer gas when the operator desires a low resolution analysis.

As can be seen, FIG. 3a, which uses a medium weight buffer gas (nitrogen), has identified fewer beats than FIG. 3b, which uses a light weight buffer gas (helium). This is a consequence of the lower resolution achieved by a medium weight buffer gas compared with a light weight buffer gas.

Figure 4A:
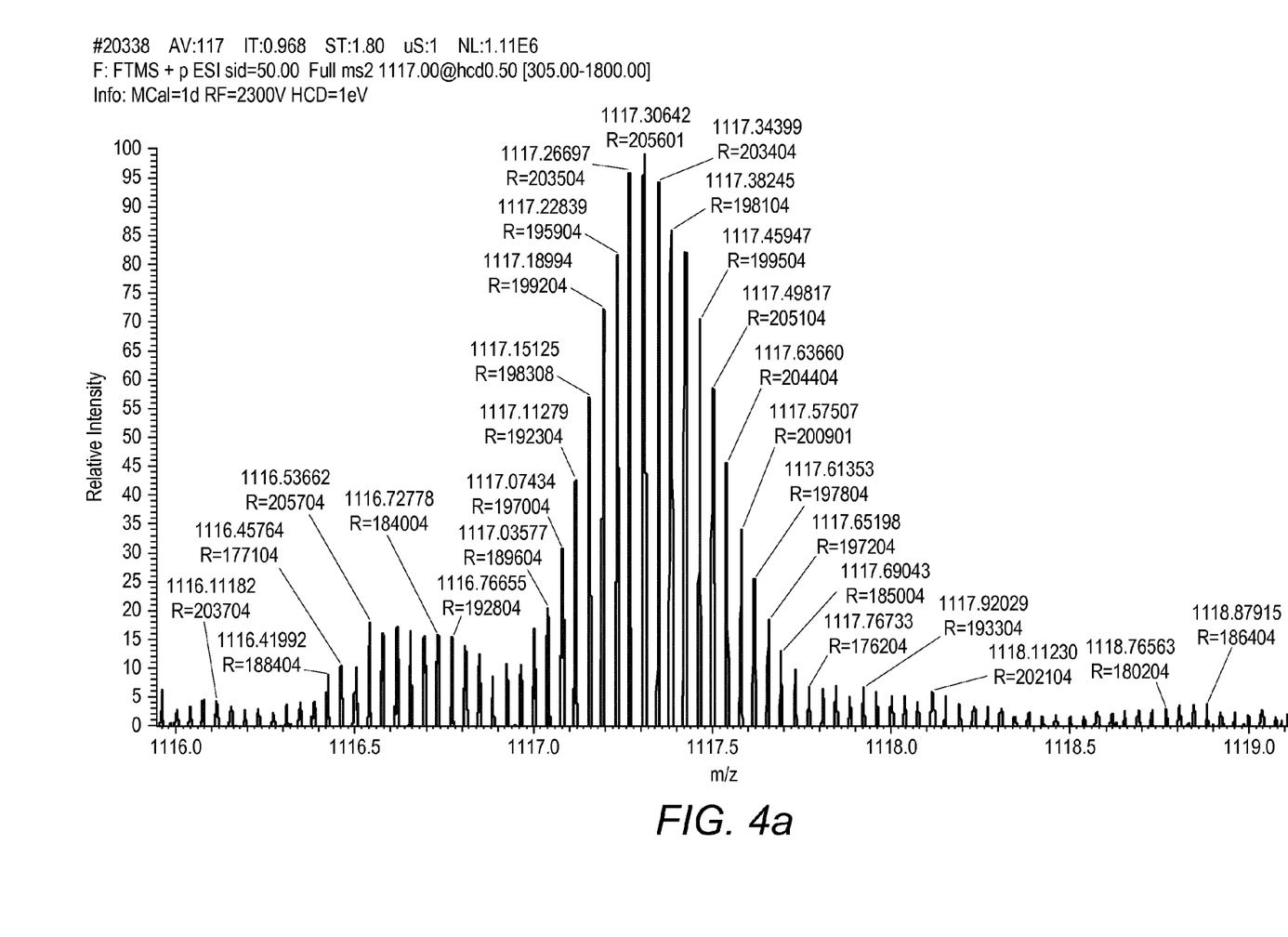
FIGS. 4a and 4b show a mass spectra obtained from one of the transients identified in FIGS. 3a and 3b.

FIG. 4a shows the mass spectra obtained from one of the transients identified in FIG. 3a.

Figure 4B:
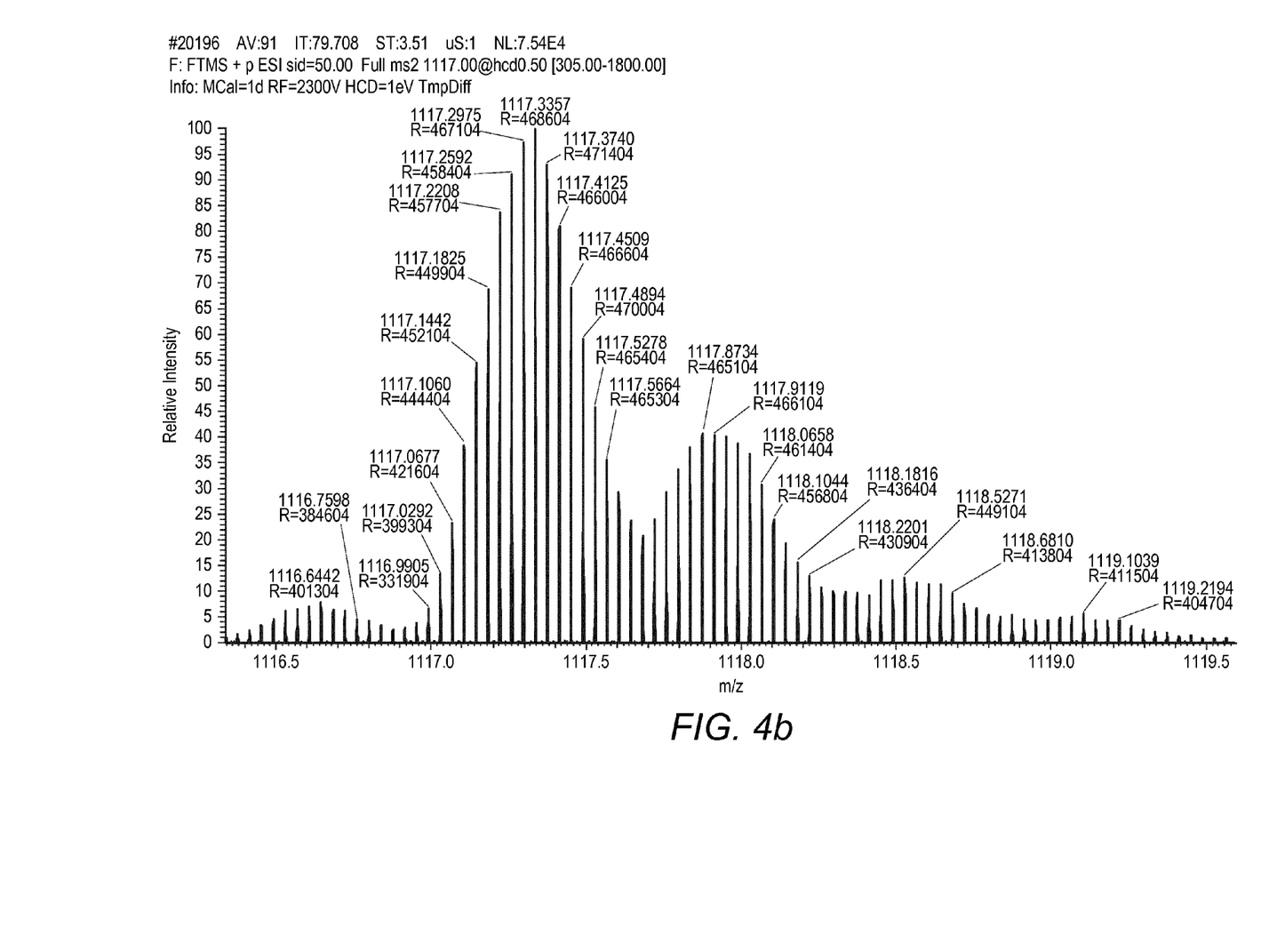

FIG. 4b shows the mass spectra obtained from one of the transients identified in FIG. 4b.

Again, it can be seen that the transient of FIG. 4b, which is obtained using a light weight buffer gas (helium), has a higher resolution than that of FIG. 4a, which is obtained using a medium weight buffer gas (nitrogen).

In an alternative arrangement of the above described mass spectrometer 101, rather than supplying the buffer gas into the HCD collision cell 145 and setting the partial pressure for the mass analyser 165, the buffer gas may instead be supplied into any other relevant optical element of the mass analyser 101 in order to achieve a desired partial pressure in any relevant optical element of the mass analyser 101. For example, the C-trap 140 may be directly supplied with a buffer gas at a gas pressure suitable to achieve the desired partial pressure in the mass analyser 165, wherein both the buffer gas selection and the partial pressure selection are controlled by the controller 180 in accordance with the method described above and shown in FIG. 2. Or, for example, gas may be directly supplied into the high pressure cell 125 at a gas pressure suitable for achieving a desired partial pressure in the high pressure cell 125.

The mass spectrometer 101 is not limited to include only those ion optical elements shown in FIG. 1, but may have fewer ion optical elements or more ion optical elements.

Figure 5:
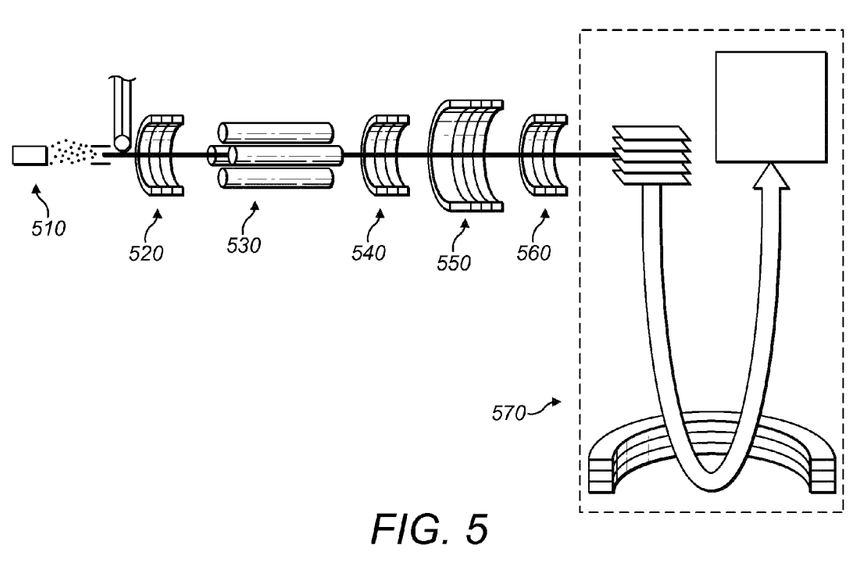
FIG. 5 shows a mass spectrometer comprising a first mass analyser, several collision and trapping devices and a time of flight mass analyser, wherein buffer gas may be supplied to any or all of the mass spectrometer components and the gas type and gas pressure may be set according the method shown in FIG. 2.

FIG. 5 shows a different example of a mass spectrometer arrangement to which the disclosed gas control process may be applied. The mass spectrometer in FIG. 5 comprises an ion source 510, a first ion guide 520, a first (quadrupole) mass analyser 530, a second guide 540 (which may also be operable as a first ion trap), a collision cell/ion mobility device 550, a third ion guide 560 (which may also be operable as a second ion trap) and a time of flight mass analyser 570. The collision cell/ion mobility device 550 may be set up to perform fragmentation in the entrance zone of the device and ion mobility separation in the elongated part of the device. The time of flight mass analyser 570 may be a single reflection time of flight mass analyser, or a multi-reflection time of flight mass analyzer.

Any one or more of the mass spectrometer elements shown in FIG. 5 may be supplied directly with buffer gas, and the buffer gas pressure(s) and/or type(s) may be selected according to the disclosed control process in order to optimise performance of the mass spectrometer. For example, adjustment of the gas pressure and/or type in the collision cell/ion mobility device 550 may affect the ion mobility performance by, for example, shifting the range of separable mobilities from 'low' to 'high' or increasing/decreasing mobility resolution. Fragmentation in the collision cell may also be modified by changes in gas pressure and/or type, so as to improve fragmentation efficiency and/or avoid unwanted fragmentation. Therefore the performance of the mass spectrometer may be improved by optimising the ion mobility performance and/or fragmentation in the collision cell for the particular characteristic of the analysis to be performed.

The performance of the first mass analyser 530 and the ion guides 520, 540 and 560 may also be affected by the gas type and pressure. The time of flight resolution of the time of flight mass analyser 570 may also be affected by changes in gas pressure and/or type, and the operation of guides 540 and 560 as ion traps (for example to improve duty cycle) may also be affected by the gas pressure and type.

Furthermore, rather than supplying gas to one ion optical element of the mass spectrometer 101, two or more different ion optical elements may be independently supplied and controlled by the controller 180. For example, the mass spectrometer 101 may be configured such that the buffer gas in one particular ion optical element does not enter a particular adjacent ion optical element so that the HCD collision cell 145 may be directly supplied with a first buffer gas from the gas supply 185 via a first pressure controller and first gas type selector and the C-trap 140 may be directly supplied (and the mass analyser 165 indirectly supplied therefrom) with a second buffer gas from the gas supply 185 via a second pressure controller and second gas type selector. The second pressure controller and gas type selector may be configured to be controlled independently of the first pressure controller and gas type selector by the controller 180.

By supplying gas to the C-trap 140 and mass analyser 165 independently from the HCD collision cell 145, a different gas may be used for the C-trap 140 and mass analyser 165 from that of the HCD collision cell 145. For example, an advantageous gas for the mass analyser 165 (such as helium) may be supplied to the C-trap 140, and an advantageous gas for specialised HCD collision cell applications (for example, ammonia for reactions in the cell, or nitrogen or sulphur hexafluoride for higher collision efficiencies) may be supplied to the HCD collision cell 145. Furthermore, it may also be possible to achieve an advantageous pressure in the second ion optical element (the HCD collision cell 145) that would be unobtainable in conjunction with an advantageous pressure in the first ion optical element (the mass analyser 165) if the two ion optical elements were not independently supplied.

Whilst the above described aspects of the disclosure suggest a limited number of gases for use as a buffer gas in the mass spectrometer 101, any gas suitable for use with mass spectrometers may be used. The gas may have a composition of only a single element or compound, or may be composed of any two or more elements and/or compounds.

In the control process shown in FIG. 2 and described above, there are three different mass ranges in which the expected mass of the sample ions may be determined to lie. However, it may be arranged that only two different mass ranges are set, or that four or more mass ranges are set, wherein the control process can determine in which of the set ranges the expected mass of the sample ions lies. The thresholds for each of the different expected mass ranges may be set to any suitable value and for each range there may be a corresponding partial pressure range setting and/or buffer gas selection.

Alternatively, the controller 180 may be configured to apply the expected mass of the sample ions to a function that determines the buffer gas and gas pressure to be used, without using mass ranges at all.

Furthermore, rather than having expected charge ranges, the control process shown in FIG. 2 and described above may instead consider any suitable characteristic of the sample ion. For example, expected sample ion charge ranges may be set and determination of the expected sample ion charge range in which the sample ions lie made to determine the characteristic of the analysis to be performed and set a suitable buffer gas and partial pressure. Likewise, rather than considering mass, expected sample ion mass to charge ratio (m/z) ranges may be set and expected sample ion m/z considered.

Furthermore, rather than having the operator of the mass spectrometer 101 inputting to the controller 180 the application of the analysis to be performed (for example, "general", "metabolomics", "bottom up proteomics", "top down proteomics" and "native MS") the operator may instead directly enter in Step S200 any other relevant information, for example the expected mass and/or energy of the sample ions. The control process may then continue from Step S205 onwards as shown in FIG. 2 and described above. Alternatively, the operator may enter information about the type of the sample to be analysed, selected from a list of possible sample types, for example "bile", "blood", "urine", "digested cell lysate", "food", "water", "cell extracts", "QC samples" etc. The expected mass and/or energy of the sample ions may then be determined in an analogous process to that described above in respect of the application of the analysis to be performed. Furthermore, a variety of information may be entered by the operator (for example the type of analysis to be performed and the expected mass of the sample) and used by the controller 180 to determine the characteristic of the analysis to be performed (for example using a function that considers all entered information).

If the operator inputs the application of the analysis to be performed and/or the type of the sample to be analysed, rather than looking up an expected mass of the sample ions and then determining the characteristic of the analysis to be performed from the expected mass of the sample ions, the controller 180 may alternatively use the entered application of the analysis to be performed and/or the type of the sample to be analysed as the characteristic of the analysis to be performed. The corresponding buffer gas and gas pressure may then be looked up for the characteristic of the analysis to be performed and the controller 180 set about applying the buffer gas and the gas pressure to the mass spectrometer 101. Alternatively, the controller 180 may be configured to identify in which expected mass range the sample ions fall merely on the basis of the entered application of the analysis to be performed and/or the type of the sample to be analysed and then perform Steps S210 onwards as described above.

The operator may be presented with various options for the sort of information that they would like to enter into the controller 180, with which the controller 180 may determine the characteristic of the analysis to be performed. For example, the operator may have the option to enter at least one of an expected mass of the sample ions, an expected charge of the sample ions, an application of the analysis of the sample ions, a type of the sample ions and a desired resolution of analysis. The operator may enter information for any one or more of these fields, using which the controller 180 can determine the characteristic of the analysis to be performed and then set the buffer gas composition and pressure accordingly. In this way, the operator has the opportunity to enter only information that is readily to hand and is not burden with needing to look up additional information or undertake calculations if they do not want to.

Furthermore, rather than receiving from the operator information used to determine the characteristic of the analysis to be performed, the controller may alternatively be configured to receive the information from any other suitable source, for example another electronic component of the mass spectrometer or any other device. For example, the mass spectrometer may begin operation in a default state without any knowledge at the controller 180 of the characteristic of the analysis to be performed. As such, the operator may begin operation of the mass spectrometer 101 without inputting any information into the controller 180. The default setting may be, for example, to set the gas pressure and gas type to that of the low expected mass range. Having set the gas pressure and gas type to the default setting, the mass analyser 101 may perform an analysis of the sample ions, for example an analysis of the mass and/or charge of the ions. On the basis of the analysis, which may be an instantaneous analysis result or analysis results averaged over a period of time, the controller 180 may determine the characteristic of the analysis to be performed by the mass spectrometer. The controller 180 may then set the gas pressure and gas type according to the determined characteristic of the analysis to be performed. This may result in a change in the gas pressure and/or gas type and the analysis of the sample ions resuming with improved mass spectrometer performance.

Even after the controller 180 has determined the characteristic of the analysis to be performed, whether from information input to the controller 180 by the operator or from the analysis process described in the above paragraph, the controller 180 may make a further determination of the characteristic of the analysis to be performed on the basis of an analysis performed by the mass spectrometer. The controller 180 may consider an instantaneous result or a plurality of results averaged over a period of time of an analysis by the mass spectrometer 101, for example of the sample mass and/or charge, and determine the characteristic of the analysis to be performed. If this newly determined characteristic is different to the previously determined characteristic, the controller 180 may change the gas pressure and/or gas type accordingly. Reconsidering the characteristic of the analysis to be performed in this way may result in an improved determination of the characteristic, for example because the previous characteristic was determined on the basis of inaccurate information input by the operator, which may result in improved mass spectrometer performance for subsequent analyses.

Whilst in the control process shown in FIG. 2 and described above, both the type of buffer gas and the partial pressure of the buffer gas are selected and controlled by the controller 180 on the basis of a characteristic of the analysis, alternatively only one of the buffer gas or the partial pressure of the buffer gas may be selected and controlled by the controller 180, with the other remaining constant for all analysis characteristics.

Whilst in the control process shown in FIG. 2 and described above, the operator is only asked for their desired resolution when the expected mass of the sample ions is in the medium expected mass range, the operator may alternatively be ask at any stage what their desired analysis resolution is, for example it may be input in Step S200. Furthermore, the desired analysis resolution may affect the characteristic of the analysis to be performed and therefore affect the selected buffer gas and gas pressure.

The mass analyser 165 may be any form of mass analyser, for example an orbital trapping mass analyser, a linear or 3D ion trap, a time of flight (TOF) mass analyser, in particular a multi-reflection TOF (MRTOF), or a Fourier transform ion cyclotron resonance (FTICR) mass analyser. Furthermore, the C-trap 140 could be any form of trap or storage device and the HCD collision cell 145 could be any form of collision cell. Furthermore, the ion source 105 may be any type of ion source, for example MALDI or atmospheric pressure ionisation (API), such electrospray (ESI), photon (APPI), chemical (APCI), or plasma (ICP, glow discharge, corona discharge).

INDUSTRIAL APPLICABILITY

The present disclosure finds application in the field of mass spectrometry.

The invention claimed is:

1. A mass spectrometer for performing an analysis of sample ions, the mass spectrometer comprising:
a first ion optical element that is supplied with a first gas;
a mass analyzer, wherein the performance of the mass analyzer is dependent on the pressure of the first gas in the first ion optical element; and
a controller for setting a property of the first gas, which comprises at least the pressure of the first gas, on the basis of at least an expected mass of the sample ions and a desired resolution of the mass analyzer, wherein setting the property of the first gas includes determining a compromise between optimizing the performance of the first ion optical element and optimizing the performance of the mass analyzer, the controller comprises a computer for making rules-based decisions for setting the property of the first gas, wherein the rules-based decisions comprise determining which of a plurality of predetermined mass ranges an expected or determined mass of the sample lies within, determining whether a desired mass resolution lies below or above a mass resolution threshold and setting the property of the gas based on the determination to enable a desired signal intensity and/or mass resolution to be obtained using the mass analyzer.

2. The mass spectrometer of claim 1, wherein the mass analyzer is selected from: an ion cyclotron resonance (ICR) mass analyzer, an orbital trap mass analyzer, a time-of-flight mass analyzer, an electrostatic trap mass analyzer, and an electrodynamic ion trap mass analyzer.

3. The mass spectrometer of claim 1, wherein the property of the first gas further comprises at least a composition of the first gas.

4. The mass spectrometer of claim 1, further comprising:
a second ion optical element that is supplied with a second gas; wherein the controller is configured for setting a property of the second gas on the basis of the characteristic of the analysis to be performed by the mass spectrometer.

5. The mass spectrometer of claim 4, wherein the property of the second gas comprises at least one of a second gas pressure in the second ion optical element and a composition of the second gas.

6. The mass spectrometer of claim 1, wherein the controller is configured to receive an input of an application of the analysis of the sample ions, a type of the sample ions, the expected mass of the sample ions, a charge of the sample ions and the desired analysis resolution.

7. The mass spectrometer of claim 6, wherein the controller is configured to receive the input of at least one of the application of the analysis of the sample ions, the type of the sample ions, the expected mass of the sample ions, the expected charge of the sample ions and the desired analysis resolution from an operator of the controller.

8. The mass spectrometer of claim 1, wherein the controller is configured to determine at least one of a type of the sample ions, the expected mass of the sample ions and an expected charge of the sample ions from a mass spectrometer experimentation result.

9. The mass spectrometer of claim 8, wherein the at least one of the type of the sample ions, the expected mass of the sample ions and the expected charge of the sample ions is determined from at least one of an average mass and average charge obtained from a plurality of mass spectrometer experimentation results.

10. The mass spectrometer of claim 1, wherein the first ion optical element is any one of a mass analyzer; a collision cell; an ion storage device; an ion guide; a mass filter; an ion mobility analyzer; and an ion lens.

11. A method for operating a mass spectrometer, the mass spectrometer comprising a first ion optical element and a mass analyzer, the method comprising the steps of:
determining at least an expected mass of sample ions and a desired resolution of the mass analyzer; and
determining whether a desired mass resolution lies below or above a mass resolution threshold, and
making a rules-based decision to determine the property of a first gas, including at least pressure of the first gas, based on said determinations to enable a desired signal intensity and/or mass resolution to be obtained using the mass analyzer, wherein determining the property of the first gas includes determining a compromise between optimizing the performance of the first ion optical element and optimizing the performance of the mass analyzer;
setting, on the basis of the rules based decision, the property of a first gas used for supplying a first ion optical element of the mass spectrometer, wherein the performance of the mass analyzer is dependent on the pressure of the first gas in the first ion optical element.

12. The method of claim 11, wherein the mass analyzer is any one of: an ion cyclotron resonance (ICR) mass analyzer, an orbital trap mass analyzer, a time-of-flight mass analyzer (especially a multiple-reflection time-of-flight (MR-TOF) mass analyzer), an electrostatic trap mass analyzer, and an electrodynamic ion trap mass analyzer.

13. The method of claim 11, wherein the property of the first gas further comprises at least a composition of the first gas.

14. The method of claim 11, further comprising the step of:
setting, on the basis of the characteristic of the sample ion, a property of a second gas used for supplying a second ion optical element of the mass spectrometer.

15. The method of claim 14, wherein the property of the second gas comprises at least one of a second gas pressure in the second ion optical element and a composition of the second gas.

16. The method of claim 11 further comprising:
receiving at least one of an application of the analysis of the sample ions, a type of the sample ions, the expected mass of the sample ions, an expected charge of the sample ions and the desired analysis resolution from an operator of the mass spectrometer.

17. The method of claim 11 further comprising:
determining at least one of a type of the sample ions, the expected mass of the sample ions and an expected charge of the sample ions from a mass spectrometer experimentation result.

18. The method of claim 17 wherein the at least one of the type of the sample ions, the expected mass of the sample ions and the expected charge of the sample ions is determined from at least one of an average mass and average charge obtained from a plurality of mass spectrometer experimentation results.

19. The method of claim 11, wherein the first ion optical element is any one of a mass analyzer; a collision cell; an ion storage device; an ion guide; a mass filter; an ion mobility analyzer; and an ion lens.

* * * * *

UNITED STATES PATENT AND TRADEMARK OFFICE
CERTIFICATE OF CORRECTION

PATENT NO. : 9,865,441 B2
APPLICATION NO. : 14/912118
DATED : January 9, 2018
INVENTOR(S) : Nicolaie E. Damoc et al.

Page 1 of 1

It is certified that error appears in the above-identified patent and that said Letters Patent is hereby corrected as shown below:

Claim 6, Column 17, Line 14:
Replace "..., a charge of the sample..."
With --..., a expected charge of the sample...--

Signed and Sealed this
Fifteenth Day of May, 2018

Andrei Iancu
*Director of the United States Patent and Trademark Office*